(12) United States Patent
Zambelli

(10) Patent No.: US 8,439,846 B2
(45) Date of Patent: May 14, 2013

(54) BONE BIOPSY DEVICE

(76) Inventor: Roberto Zambelli, Milan (IT)

( * ) Notice: Subject to any disclaimer, the term of this patent is extended or adjusted under 35 U.S.C. 154(b) by 712 days.

(21) Appl. No.: 12/622,565

(22) Filed: Nov. 20, 2009

(65) Prior Publication Data
US 2010/0204611 A1 Aug. 12, 2010

(30) Foreign Application Priority Data

Feb. 6, 2009 (EP) .................................... 09425041

(51) Int. Cl.
- *A61B 10/00* (2006.01)
- *A61B 17/32* (2006.01)
- *A61B 17/14* (2006.01)

(52) U.S. Cl.
USPC ........................ 600/567; 606/167; 606/184

(58) Field of Classification Search .......... 600/562–568; 606/167, 184
See application file for complete search history.

(56) References Cited

U.S. PATENT DOCUMENTS

| | | | | |
|---|---|---|---|---|
| 1,867,624 A * | 7/1932 | Hoffman | .................. | 600/567 |
| 3,929,123 A * | 12/1975 | Jamshidi | .................. | 600/567 |
| 4,785,826 A * | 11/1988 | Ward | .................. | 600/567 |
| 5,257,632 A | 11/1993 | Turkel et al. | | |
| 5,333,619 A * | 8/1994 | Burgio | .................. | 600/567 |
| 5,357,974 A * | 10/1994 | Baldridge | .................. | 600/567 |
| 5,462,062 A * | 10/1995 | Rubinstein et al. | .................. | 600/567 |
| 5,522,398 A * | 6/1996 | Goldenberg et al. | .................. | 600/567 |
| 5,595,186 A * | 1/1997 | Rubinstein et al. | .................. | 600/567 |
| 5,634,473 A * | 6/1997 | Goldenberg et al. | .................. | 600/567 |
| 5,807,277 A * | 9/1998 | Swaim | .................. | 600/567 |
| 5,885,226 A * | 3/1999 | Rubinstein et al. | .................. | 600/564 |
| 5,910,121 A * | 6/1999 | Paolo et al. | .................. | 600/562 |
| 6,015,391 A * | 1/2000 | Rishton et al. | .................. | 600/567 |
| 6,063,037 A * | 5/2000 | Mittermeier et al. | .................. | 600/567 |
| 6,110,128 A * | 8/2000 | Andelin et al. | .................. | 600/566 |
| 6,416,484 B1 * | 7/2002 | Miller et al. | .................. | 600/564 |

(Continued)

FOREIGN PATENT DOCUMENTS

| | | |
|---|---|---|
| EP | 1 136 039 A2 | 9/2001 |
| EP | 1175866 A | 1/2002 |

(Continued)

OTHER PUBLICATIONS

European Search Report in Corresponding Application EP 09 42 5041 dated Jul. 7, 2009.

(Continued)

*Primary Examiner* — Max Hindenburg
*Assistant Examiner* — John Pani
(74) *Attorney, Agent, or Firm* — Young & Thompson

(57) ABSTRACT

A bone biopsy device includes an outer cannula having a mouth with a cutting edge to section a frustule of spongy bone, a plate mounted slidably within the cannula and provided with a semi-cylindrical portion at its distal end, and a stylet mounted slidably within the plate and provided with a pointed tip which protrudes from the mouth of the cannula to pierce the compact part of the bone. The mouth of the cannula has on its inside a narrowing and the semi-cylindrical part of the plate has at its distal end at least one pair of opposed circumferential sets of teeth adapted to bend radially inwards when they encounter the narrowing of the mouth, to clasp the base of the sectioned frustule and allow extraction of the frustule by the plate while the cannula is kept at the operating site, allowing aspiration of marrow after the frustule has been removed.

20 Claims, 10 Drawing Sheets

U.S. PATENT DOCUMENTS

| | | | |
|---|---|---|---|
| 6,827,692 B2 * | 12/2004 | Castellacci | 600/567 |
| 7,201,722 B2 * | 4/2007 | Krueger | 600/564 |
| 7,572,263 B2 * | 8/2009 | Preissman | 606/94 |
| D647,202 S * | 10/2011 | Scifert | D24/146 |
| 8,088,081 B2 * | 1/2012 | Field et al. | 600/567 |
| 2007/0123890 A1 | 5/2007 | Way et al. | |
| 2008/0058674 A1 | 3/2008 | Jansen et al. | |

FOREIGN PATENT DOCUMENTS

| | | |
|---|---|---|
| EP | 1 210 911 A2 | 6/2002 |
| EP | 1 277 440 A1 | 1/2003 |
| WO | WO 95/18568 A1 | 7/1995 |
| WO | WO 96/27330 A1 | 9/1996 |
| WO | WO 00/10465 A1 | 3/2000 |
| WO | 2008/068592 A | 6/2008 |

OTHER PUBLICATIONS

European Search Report in Corresponding Application EP 09 42 5041 dated Aug. 24, 2009.

* cited by examiner

BONE BIOPSY DEVICE

The present invention refers to the field of bone biopsy.

In simplified terms, the bone consists of a hard (compact or cortical) outer part and a porous (spongy or trabecular bone) inner part containing the marrow in its pores. Bone biopsy consists in sampling the inner part of the bone to ascertain the nature and development of blood cells (haemopoiesis). By removing an inner fragment of bone, in the form of a cylindrical plug (frustule), the cells in their various stages of maturation, useful for diagnosing haemato-oncological diseases, are removed therewith.

Various types of bone biopsy devices adapted to remove a frustule of spongy tissue for subsequent laboratory diagnostic tests are commercially known.

A bone biopsy device generally comprises a cylindrical cannula with a sharpened, cutting mouth within which is disposed a mandrel or stylet provided with a perforating tip which protrudes from the cannula mouth to pierce the compact bone. Once the tip of the stylet has pierced the compact bone, the stylet is extracted from the cannula and the cannula is advanced into the spongy bone, so as to section a frustule of spongy bone in the mouth of the cannula. At this point the physician carries out a rocking movement of the cannula to break the base of the frustule (luxation) that is to be removed. The cannula is then extracted from the bone, carrying the sectioned frustule inside it. Finally, an extraction rod (probe) is inserted into the mouth of the cannula to push the removed frustule towards the rear of the cannula and cause it to exit the instrument.

Such a bone biopsy system presents various drawbacks. The main drawback is due to the numerous frustules which are lost when they slip out of the mouth of the cannula as it is extracted from the patient.

Another drawback is represented by the fact that besides collecting the frustule, the physician generally has to sample marrow (blood) from inside the bone. In current biopsy instruments, this blood sampling must obligatorily be done before sectioning the frustule, otherwise the previously sectioned frustule would obstruct the mouth of the cannula, preventing aspiration of the marrow. As a result, the frustule that will subsequently be made will be deprived of blood cells which are important for the diagnostic examination. Consequently, the physician frequently has to perform two separate samplings with two different instruments: one for marrow sampling and the other for frustule sampling.

To overcome at least in part the drawback of frustule losses, cannulae are known on the market with a frustoconical shaped mouth. In this manner, the cylindrical frustule sectioned by the cutting edge of the mouth of the cannula, thanks to the luxating movement, comes to rest on the tapered inner wall of the mouth and is disposed with an oblique axis with respect to the axis of the mouth, occupying a space greater than the outlet diameter of the mouth, thus avoiding falling through the hole in the mouth.

However this system does not completely eliminate loss of frustules. Furthermore, because of the tapered tip, which increases the diameter of the cannula, generally up to 4-5 mm or more, and the luxating movement to break the base of the frustule, bone biopsy proves to be a very invasive, traumatic and painful procedure for the patient.

U.S. Pat. No. 5,333,619 in the name of Burgio describes a plate-shaped device, having a semi-cylindrical tip, which will henceforth be called a plate. The plate is inserted in the cannula having a tapered mouth, after luxation to sever the base of the frustule. The tip of the plate bends, encountering the tapered walls of the cannula mouth and is wedged between the frustule and the walls of the mouth, preventing loss of the frustule. However, with this plate device frustule loss has not been eliminated completely. Furthermore insertion of the plate into the biopsy cannula sometimes pushes the frustule, damaging it or breaking it into a number of fragments.

An alternative to the plate device was disclosed in WO95/18568 (Medsol) which describes an inner cannula having a spiral-shaped end which, when put under traction is tightened, gripping the sectioned frustule in the mouth of the outer cannula and allowing it to be detached. This device presents some drawbacks due mainly to the fact that the frustule squeezed by the coil is damaged and that, to ensure the necessary space for the inner system, the outer cannula has an increased outer diameter resulting in greater trauma for the patient.

To decrease the trauma to the patient and avoid damaging the frustule, biopsy devices are known such as that described in EP 1 210 911 (Islam) and EP 1 277 440 (Zambelli), which provide a cylindrical mouth with an inner diameter smaller than that of the cannula, so as to define a edge able to retain the frustule.

In any case, all the above mentioned devices provide for removal of the outer cannula with the captured frustule from the operating site.

Various solutions have been proposed to allow the frustule to be removed from the mouth of the outer cannula whilst still leaving it in place.

WO 96/27330 (Rubistein) describes a plate provided in the tip with tow longitudinal wings which bend inside the tapered mouth of the cannula to grip the frustule.

WO 00/10465 describes a plate provided with a tip with a slot, to improve the bending elasticity thereof. When the tip of the plate encounters the tapered mouth of the cannula, it narrows to grip the frustule.

EP 1 136 039 describes a plate provided with a tip with a narrowing, acting as a hinge, in order to bend on contact with the tapered wall of the mouth of the cannula so as to from a hook adapted to sample a portion of frustule.

These solutions have yielded very poor results, since they damage the frustule, they deform it with respect to its cylindrical shape, and they are unable to grip it firmly or they only allow partial removal of the frustule from the cannula. Furthermore, provision of the conical mouth and of luxation continues to imply the problem of a greater trauma for the patient, besides the need for an additional manoeuvre with a probe for removal from the cannula of the sampled frustule.

Object of the present invention is to overcome the drawbacks of the prior art by providing a bone biopsy device that is safe, reliable and is not traumatic or invasive for the patient.

Another object of the present invention is to provide such a device that is able to perform sampling of a frustule of bony tissue, without damage thereto.

Another object of the present invention is to provide such a device that allows removal of the frustule whilst leaving the cannula in place, thus allowing aspiration of the bone marrow after and not before sectioning the frustule.

Another object of the present invention is to provide such a device that is compact and simple and rapid to use for the physician.

These objects are achieved in accordance with the invention with the characteristics listed in appended independent claim 1.

Advantageous embodiments of the invention are apparent from the dependent claims.

The term proximal will henceforth be used to identify the parts of the device destined to face towards the operator, whereas the term distal denotes the parts of the device destined to face towards the patient during the procedure.

The bone biopsy device according to the invention comprises:

an external cannula provided with a mouth with a cutting edge to section a frustule of the spongy part of the bone,
a plate mounted slidably in the cannula and provided with a semi-cylindrical portion at its distal end, and
a stylet (or mandrel) mounted slidably inside the plate and provided with a pointed tip which protrudes from the mouth of the cannula to pierce the compact part of the bone.

The mouth of the cannula has on its inside a narrowing and the semi-cylindrical part of the plate has at its distal end at least a pair of opposed circumferential sets of teeth adapted to bend radially inwards when they encounter the narrowing of the mouth, so as to clasp the base of the sectioned frustule and allow extraction of the frustule by means of the plate whilst maintaining the cannula in the operating site.

Further characteristics of the invention will be made clearer by the detailed description that follows, referring to a purely exemplifying and therefore non limiting embodiment thereof, illustrated in the appended figures, wherein.

Figure 1:
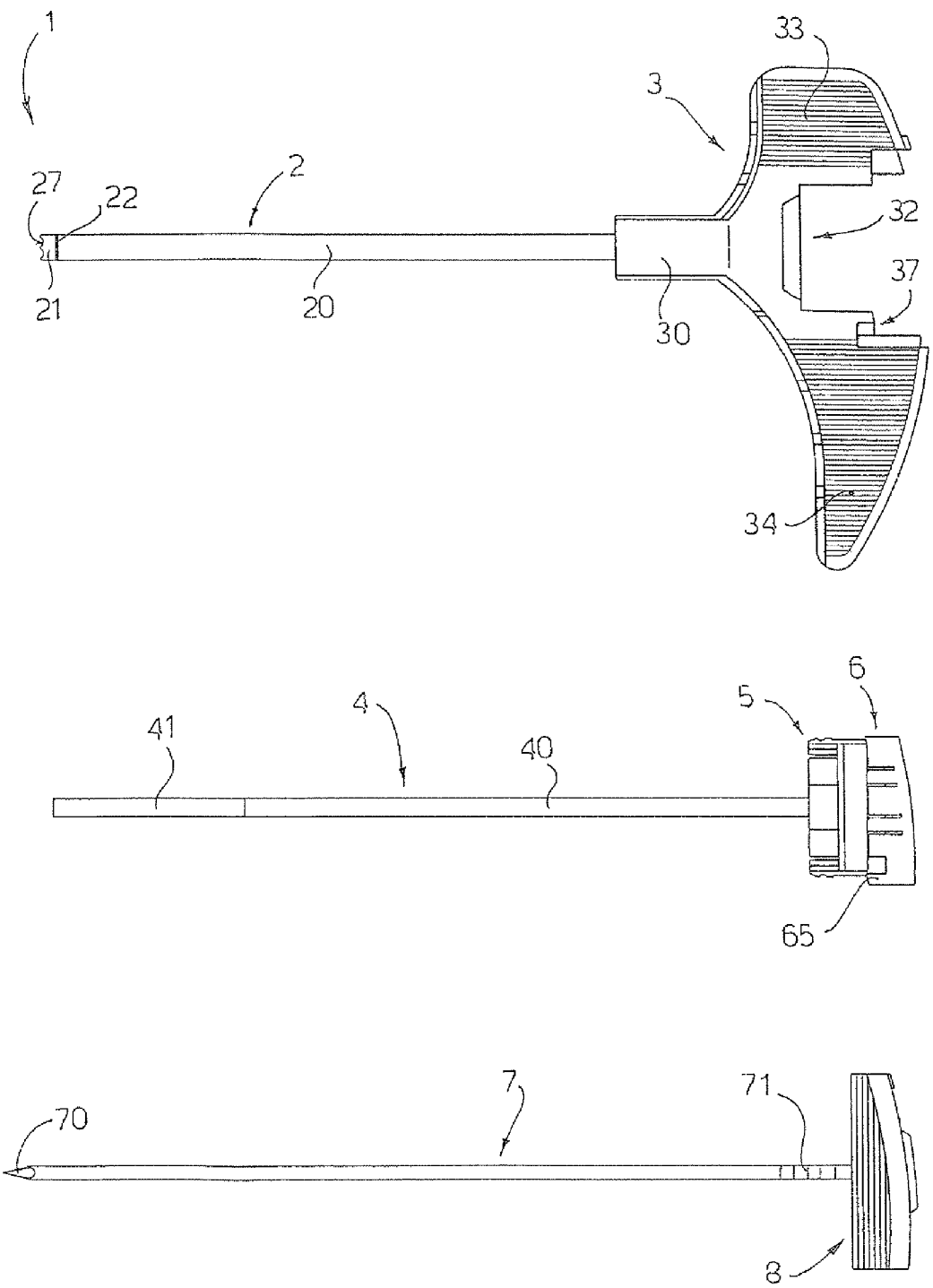
FIG. 1 is a side view illustrating the three components of the biopsy device according to the invention exploded.

The device for bone biopsy and bone marrow aspiration according to the invention, designated as a whole with reference numeral 1, is described with the aid of the figures.

With reference for now to FIG. 1, the device 1 comprises an outer cannula 2, a plate 4 adapted to be inserted axially inside the cannula 2, and a stylet or mandrel 7 adapted to be inserted axially into the plate 4.

The proximal end of the cannula 2 is fixed to a handgrip 3. The proximal end of the plate 4 is fixed to a support 5 on which is mounted a latch 6. The proximal end of the stylet 7 is fixed to a closing support 8.

Figure 2:
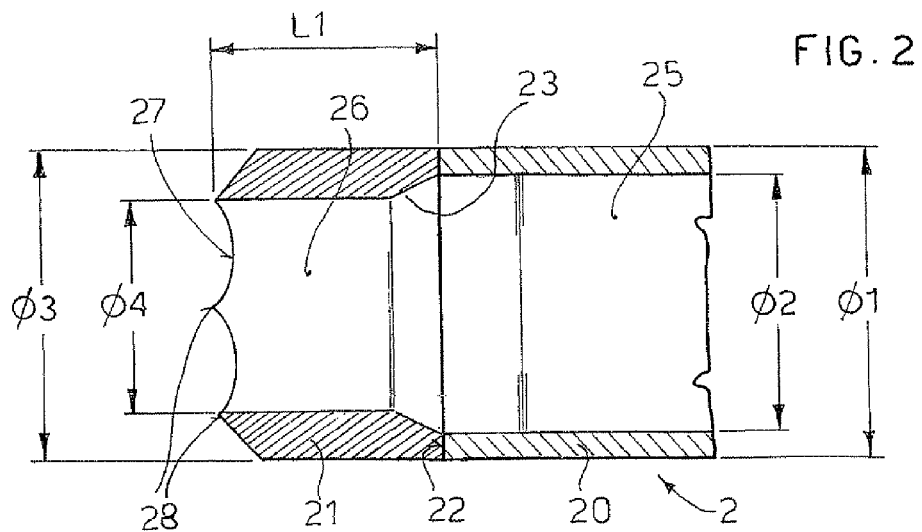
FIG. 2 is an enlarged axial sectional view, illustrating the mouth of the cannula of the device of FIG. 1.

The cannula 2 consists of a cylindrical metal tube 20, hollow on the inside so as to define an axial channel 25 (FIG. 2). As shown in FIG. 2, the cannula tube 20 has an outer diameter $\phi 1$ and an inner diameter $\phi 2$.

A mouth 21 is fixed, by laser welding 22, on the edge of the distal end of the cannula tube 20. The mouth 21 has a hollow cylindrical shape so as to define an axial chamber 26. The mouth 21 has an outer diameter $\phi 3$, an inner diameter $\phi 4$ and a length L1.

The outer diameter $\phi 3$ of the mouth 21 is equal to the outer diameter $\phi 1$ of the cannula tube 20. The inner diameter $\phi 4$ of the mouth 21, on the other hand, is slightly smaller than the inner diameter $\phi 2$ of the cannula tube 20. In this manner, a narrowing is defined in the passage from the channel 25 of the tube 20 to the chamber 26 of the mouth 21. The proximal end of the mouth 21 has a suitably flared portion 23. In this manner, the narrowing between the channel 25 of the tube 20 and the mouth 21 of the cannula is defined by a short tapered transition area 23.

The mouth 21 has a distal end edge 27 suitably tapered so as to be sharp and cutting in order to be able to penetrate the bone. The cutting edge 27 of the mouth has a profile with a plurality of adjacent arcs of a circle, so as to define a plurality of tips 28 able to scratch and cut the bone. The total length L1 of the mouth 21 is about 2-3 mm.

Figure 3:
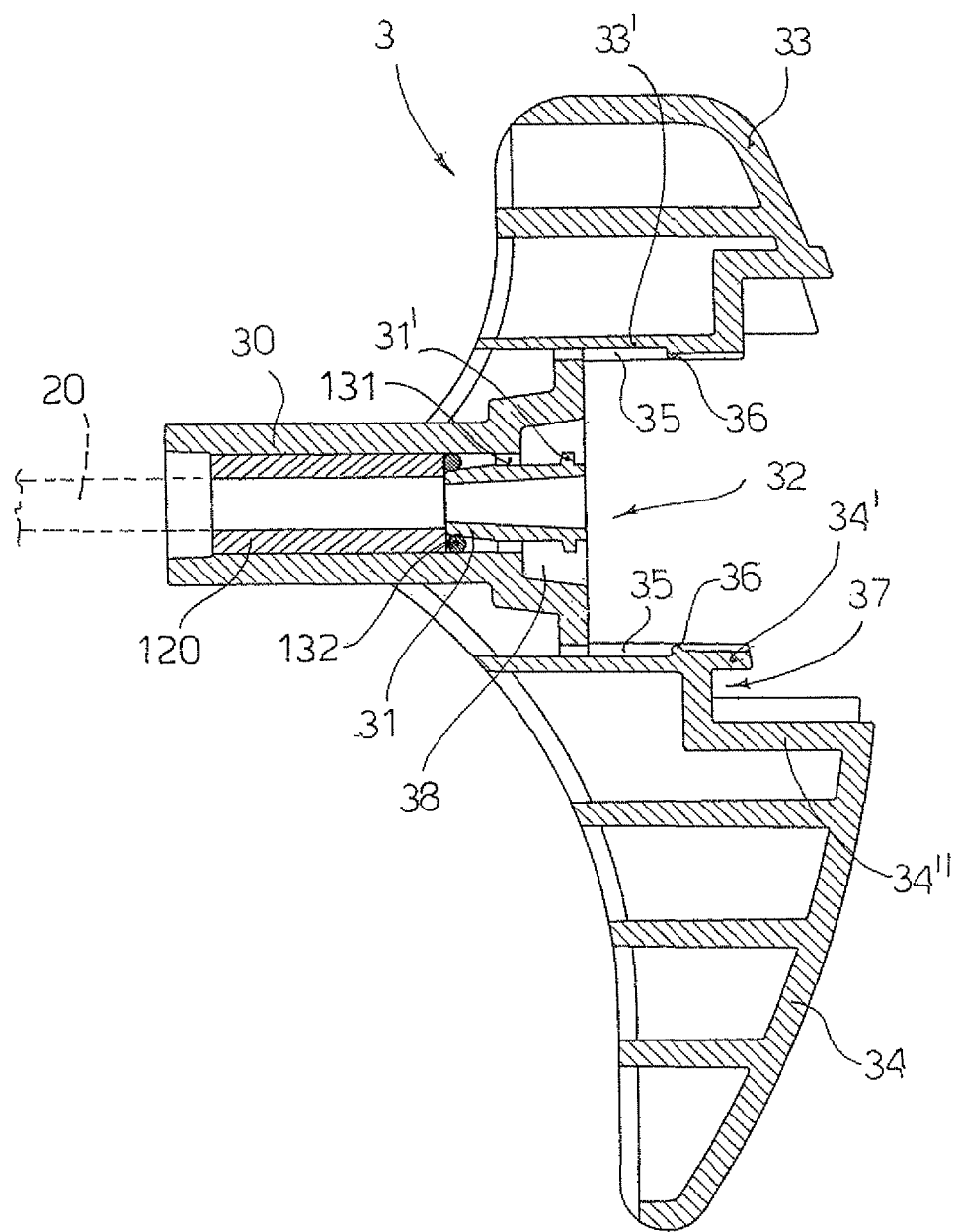
FIG. 3 is an axial sectional view of the handgrip of the device of FIG. 1.

With reference to FIGS. 1 and 3, the handgrip 3 has a cylindrical tang 30 in which is fixed, by gluing, co-moulding in plastic or another method, a metal cylinder 120 inside which is welded the proximal end part of the tube 20 of the cannula. A conical connector 31 of the Luer Lock type is provided in the proximal end of the tang 30 of the handgrip. The conical connector 31 has two radial wings 31' disposed in diametrically opposite positions, serving as a thread to allow the tip of a medical instrument, such as a syringe for bone marrow aspiration, to be screwed on.

It should be noted that the Luer Lock cone 31 is obtained by moulding directly in the handgrip 3. For this purpose, beneath the wings 31' of the Luer Lock cone there are left two side holes 131 which are closed by a ring 132 which is pressed into the seat provided for this purpose, during assembly of the instrument. This solution allows a considerable lowering of costs, compared with the prior art in which the Luer Lock cone is obtained as an extension of the metal cylinder welded to the proximal end of the biopsy cannula.

Two portions 33 and 34 of the handgrip depart in diametrically opposite directions from the tang 30. The second portion 34 of the handgrip is longer than the first portion 33 and has a curved profile so as to obtain an ergonomic handgrip.

At the proximal end of the tang 30, between the two portions 33 and 34 of the handgrip, a seat 32 is defined able to accommodate the plate support 5 and the latch 6. The seat 32 is defined between two opposite walls 33' and 34' of the handgrip portions 33 and 34. Respective guide grooves 35 which have a locking protrusion 36 are formed in the walls 33' and 34'.

In the second portion of handgrip 34, behind the wall 34', is formed a seat 37, U-shaped in cross section, disposed between the part 34' and a second part 34" of the portion of handgrip 34.

Figure 4:
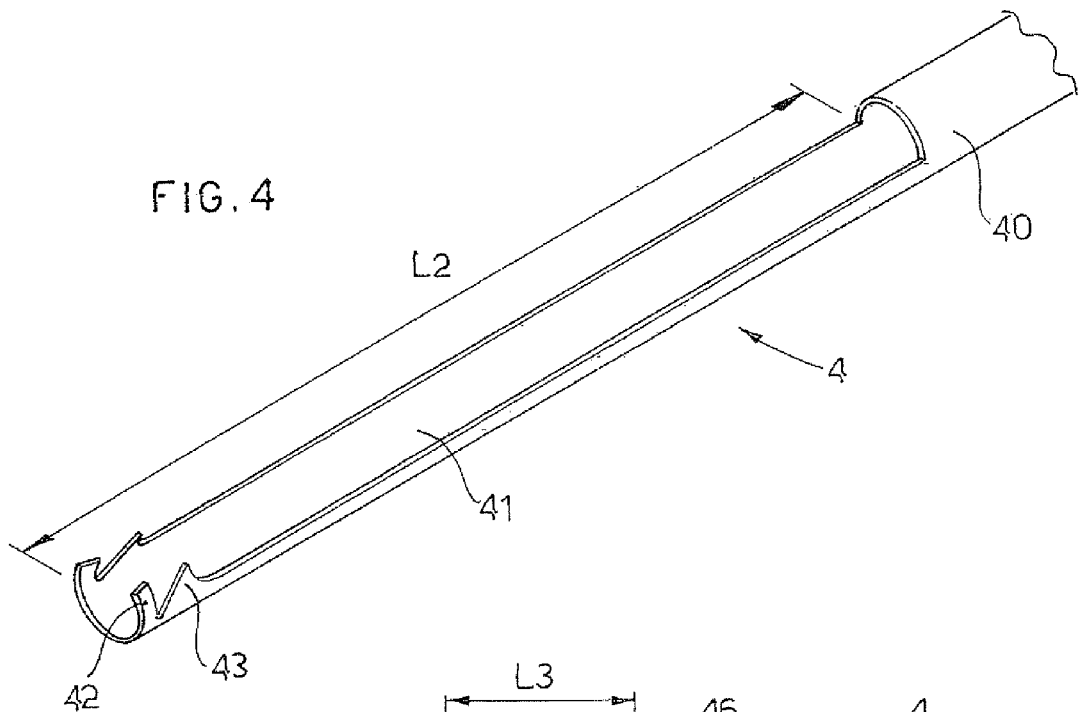
FIG. 4 is a perspective view illustrating a portion of the distal end of the plate of the device of FIG. 1.
Figure 5:
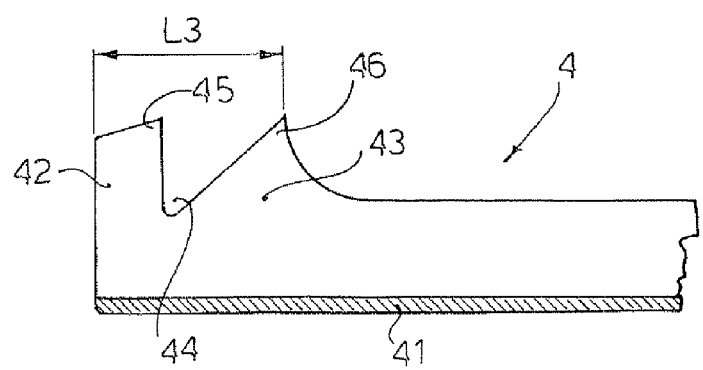
FIG. 5 is an enlarged axial sectional view of the distal end of the plate of FIG. 4.

With reference to FIGS. 1, 4 and 5, the plate 4 consists of a metal tube 40 with an outer diameter slightly smaller than the inner diameter φ2 tube 20 of the cannula, so as to be able to slide guided coaxially inside the tube 20 of the cannula. A portion of distal end of the tube 40 of the plate is cut axially for a length L2, so as to obtain a substantially semi-cylindrical portion 41. The semi-cylindrical portion 41 has a length L2 of about 3-4 cm. At the distal end of the semi-cylindrical portion 41 of the plate are formed circumferential sets of teeth 42, 43, in pairs disposed in diametrically opposite positions.

The first pair of teeth 42 is disposed at the distal end of the plate. As better shown in FIG. 5, each tooth 42 has a slightly trapezoidal profile so as to define a tip 45. The teeth 43 of the second pair have a substantially triangular profile so as to define a tip 46. Between the tooth 42 of the first pair and the tooth 43 of the second pair a substantially V-shaped notch 44 is formed. The distance of the tip 46 of the second tooth 43 from the distal end of the plate has a length L3 comparable to the length L1 of the cannula mouth.

Figure 6:
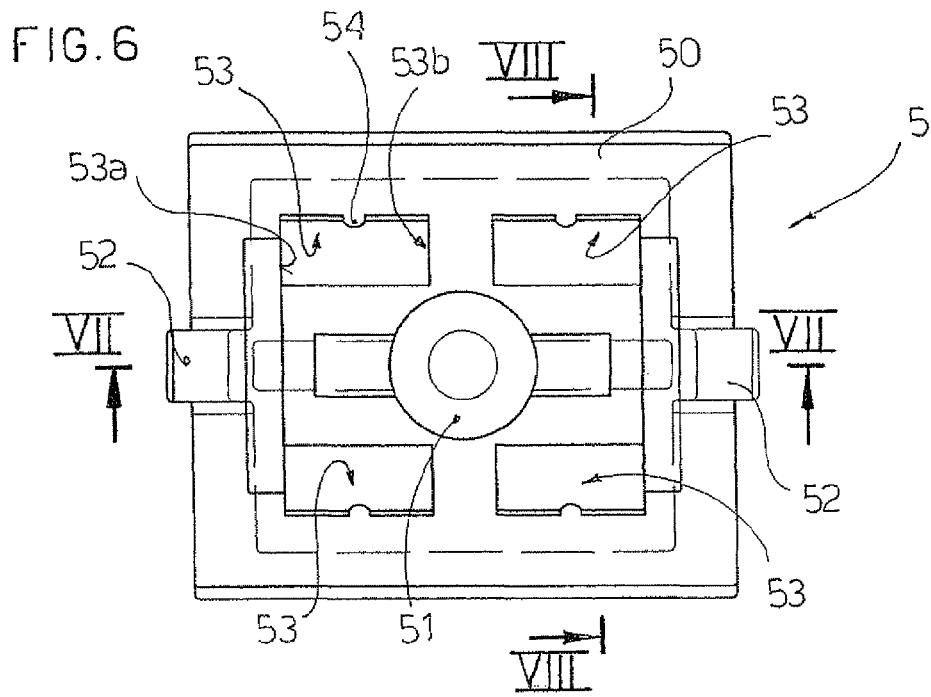
FIG. 6 is a view from the rear of the support of the plate of the device of FIG. 1.
Figure 7:
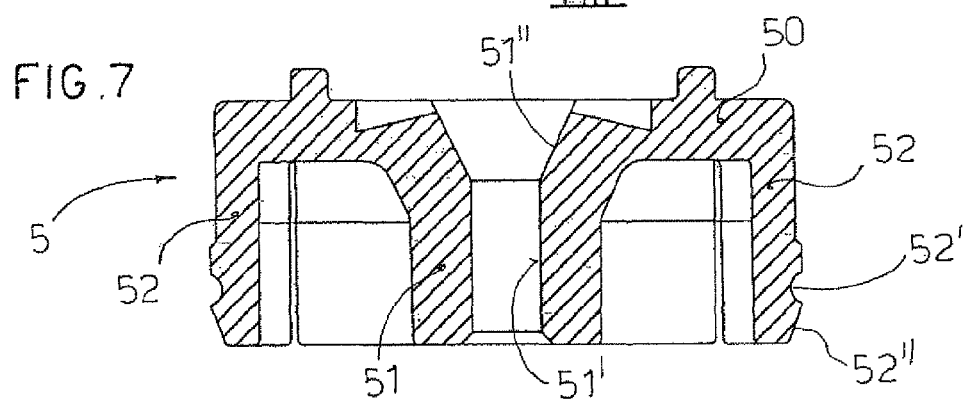
FIGS. 7 and 8 are two sectional views taken respectively along the horizontal planes of section VII-VII and VIII-VIII of FIG. 6.
Figure 8:
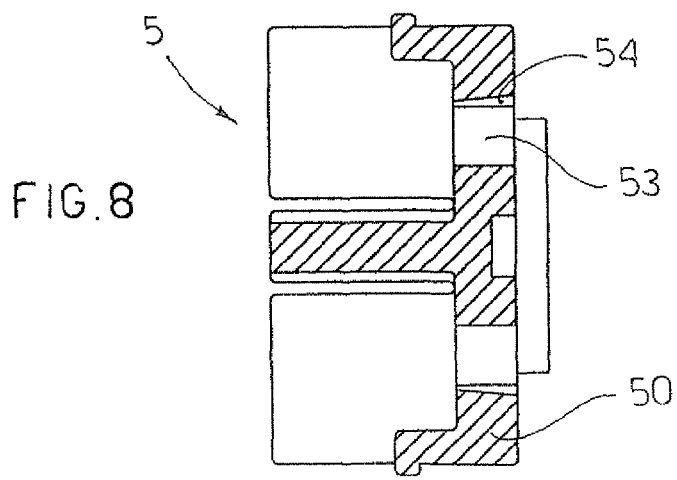

With reference to FIGS. 6, 7 and 8, the support 5 of the tube 40 of the plate comprises a body 50 substantially shaped as a rectangular plate. A tang 51 is formed in the centre of the body 50, defining a hole 51' provided with a tapered portion 51". The proximal end of the tube 40 of the plate is blocked in the hole 51, for example by depositing a suitable drop of glue in the flared part 51" of the tang 51.

Two flexible wings 52 disposed in diametrically opposite directions with respect to the tang 51 are situated at the edges of the two minor sides of the body 50. A groove 52' is formed in the outer surface of the wings 52. The surface 52" of the end part of each wing 52 is suitably tapered. In this manner, when the support 5 is inserted in the seat 32 of the handgrip 3, the flexible wings 52 of the support slide in the guide grooves 35 of the handgrip, bending inwards, until the grooves 52' of the wings of the support 5 are snap engaged by the stopping ribs 36 of the handgrip.

Four slots 53 are formed in the body 50 of the support 5. Each slot 53 defines a rear abutment edge 53a and a front abutment edge 53b. A protrusion 54, disposed in an intermediate position, is formed on a longitudinal edge of each slot 53.

Figure 9:
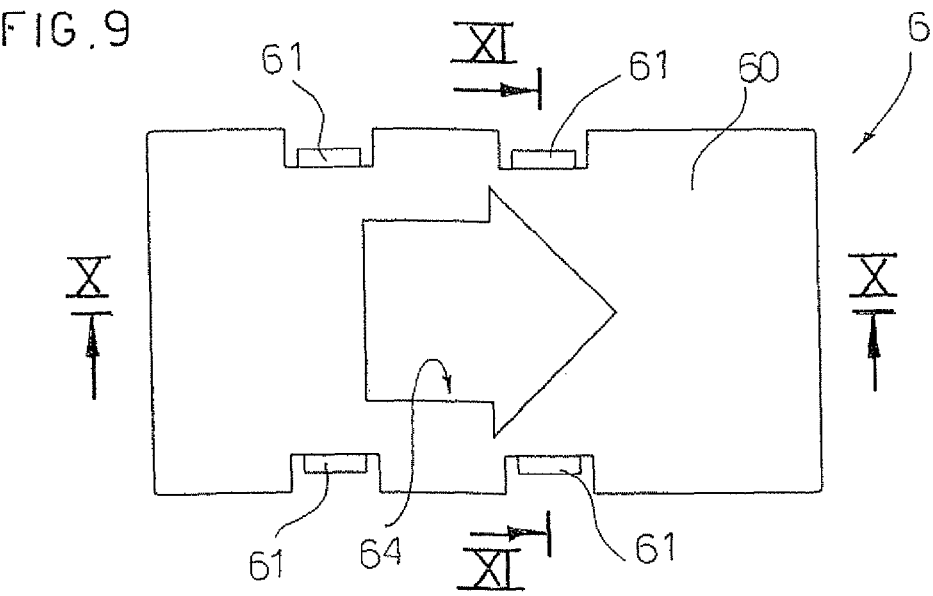
FIG. 9 is a view from the rear of the latch mounted on the support of the plate of the device of FIG. 1.
Figure 10:
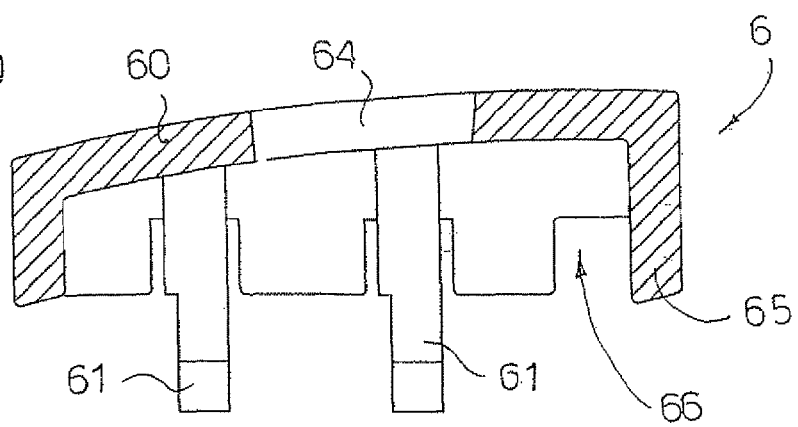
FIGS. 10 and 11 are two sectional views taken respectively along the horizontal planes of section X-X and XI-XI of FIG. 9.
Figure 11:
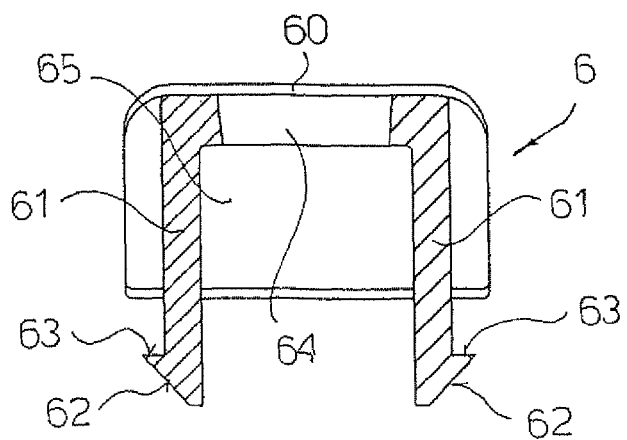

With reference to FIGS. 9, 10 and 11, the latch 6 comprises a substantially rectangular, slightly curved body 60. The body 60 of the latch is slightly longer and slightly narrower than the body 50 of the support 5. Four flexible wings 61 are formed in the edges of the two major sides of the body 60 of the latch, two on each side. Each flexible wing 61 has a tapered end 62 which defines a retaining surface 63. In this manner, the wings 61 of the latch can engage in the respective slots 53 of the support 5 and the latch 6 is retained on the support 5 by means of the retaining surfaces 63 of the wings 61 which abut against the edges of the slots 53 of the support.

An arrow 64 which indicates the direction of operation of the latch 6 to be able to arm the biopsy device 1 is formed on the body 60 of the latch. A blocking rib 65 which defines a U-shaped groove 66 is provided in the side edge of the body 60 pointed at by the arrow 64.

When the latch 6 is in the closing position, its wings 61 abut against the rear abutment surface 53a of the slots 53 of the support and do not overcome the intermediate protrusion 54 in the respective slot 53 of the support. In this situation the U-shaped groove 66 of the latch is covered by the body of the support 5 and the rib 65 of the latch is level with the wall 34' (FIG. 3) of the seat 32 of the handgrip. Consequently, the latch 6 integral with the support 5 of the plate cannot be pushed into the seat 32 of the handgrip.

On translating the latch in the direction of the arrow 64, the wings 61 of the latch slide in the slots 53 of the support, going beyond the intermediate protrusion 54 of the slots and abutting against the front wall 53b of the slot 53. As a result, the U-shaped groove 66 of the latch protrudes with respect to the body of the support 5, placing itself in register with the wall 34' of the handgrip and the rib 65 of the latch is situated level with the seat 37 of the handgrip. In this manner, the assembly formed by the support 5 and the latch 6 can be pushed into the seat 32 of the handgrip.

Figure 12:
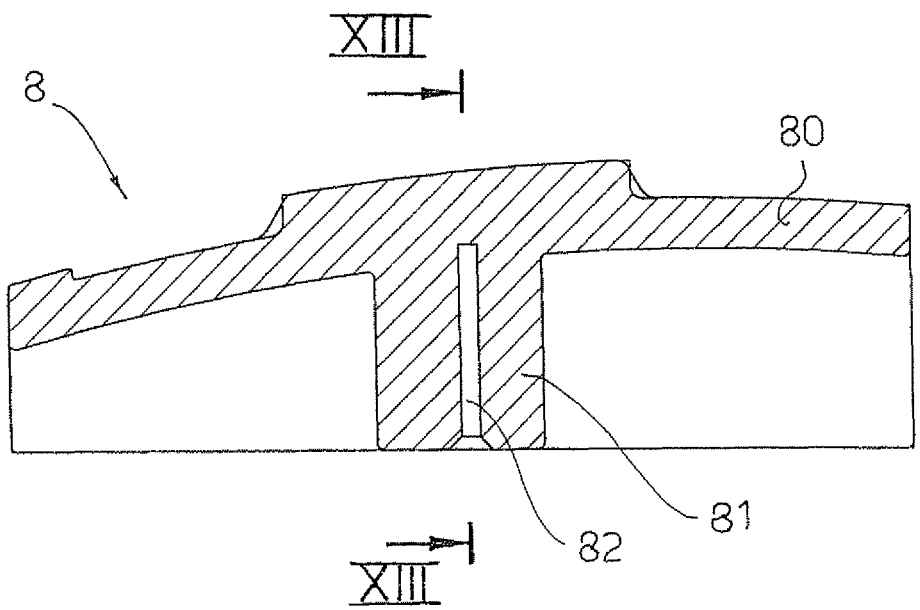
FIG. 12 is a longitudinal sectional view of the support of the stylet of the device of FIG. 1.
Figure 13:
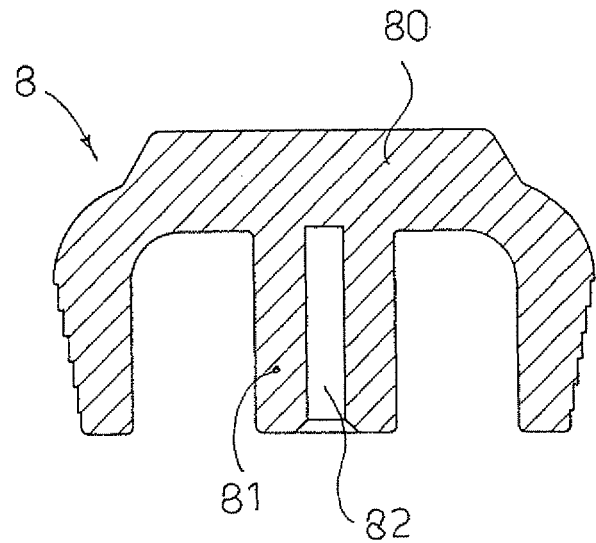
FIG. 13 is a cross sectional view, taken along the plane of section XIII-XIII of FIG. 12.

With reference to FIGS. 12 and 13, the closing support 8 comprises a substantially rectangular body 80, slightly curved so as to continue the radius of curvature that joins the two portions 33 and 34 of the handgrip. In this manner the closing support 8 acts as a cover and perfectly covers the latch 6. A tang 81 provided with a hole 82 in which is fixed the proximal end of the stylet 7 is formed in the central part of the body 80.

Operation of the bone biopsy device 1 is described with reference in particular to FIGS. 14-18.

Figure 14:
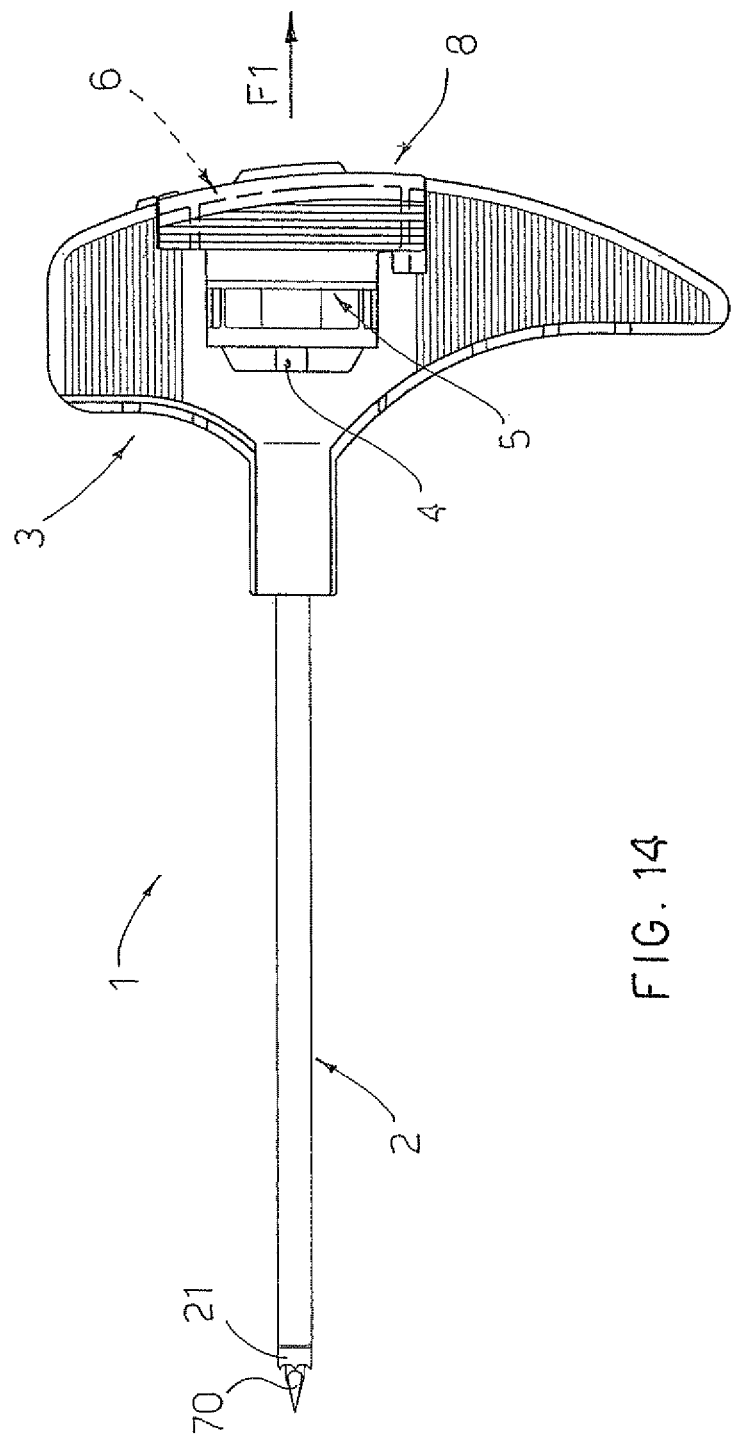
FIG. 14 is a side view of the bone biopsy device of FIG. 1 assembled, in position ready to pierce the bone.
Figure 15:
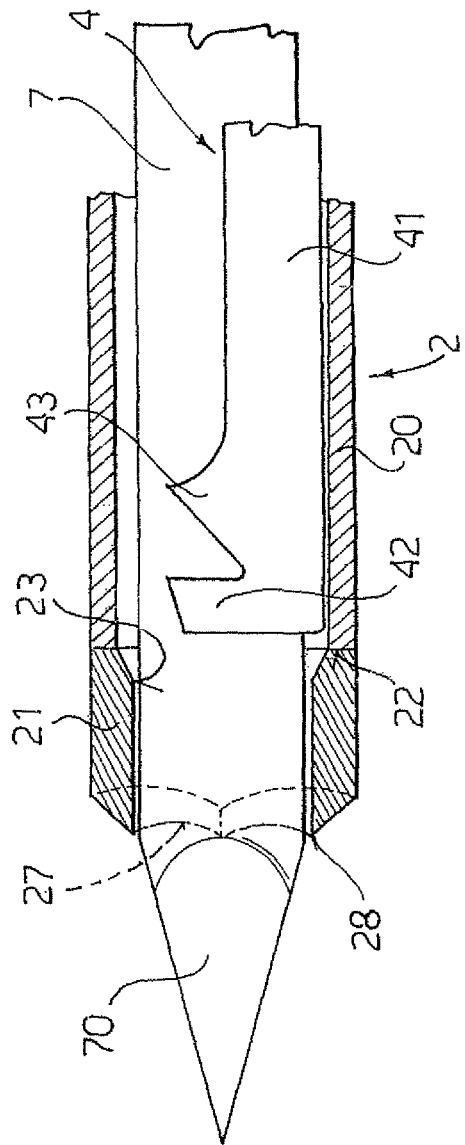
FIG. 15 is an enlarged view of the tip of the device of FIG. 14, in which the mouth of the cannula is shown in axial section.

As shown in FIGS. 14 and 15, the device 1 is initially provided in compact mode, with the plate 4 disposed inside the outer cannula 2 and the stylet 7 disposed inside the plate 4. In this condition the tip 70 of the stylet protrudes from the mouth 21 of the cannula. The teeth 42, 43 disposed at the distal end of the plate 4, on the other hand, are inside the cylindrical part 20 of the cannula, near the end of joining 22 with the mouth 21 of the cannula. The latch 6 is in a closed position, thus the plate 4 cannot move from the position illustrated.

The physician grips the handgrip 3 and carries out perforation of the compact part of the bone, by means of the tip 70 of the stylet, which acts as a guide for the cutting edge 27 of the mouth. When the mouth 21 arrives in proximity to the spongy part of the bone, the physician grips the closing support 8 and pulls it in the direction of the arrow F1, so as to extract the stylet 7. At this point the surgeon can advance the device 1 further, so that the mouth 21 of the cannula resects a cylindrical frustule of spongy bone.

Figure 16:
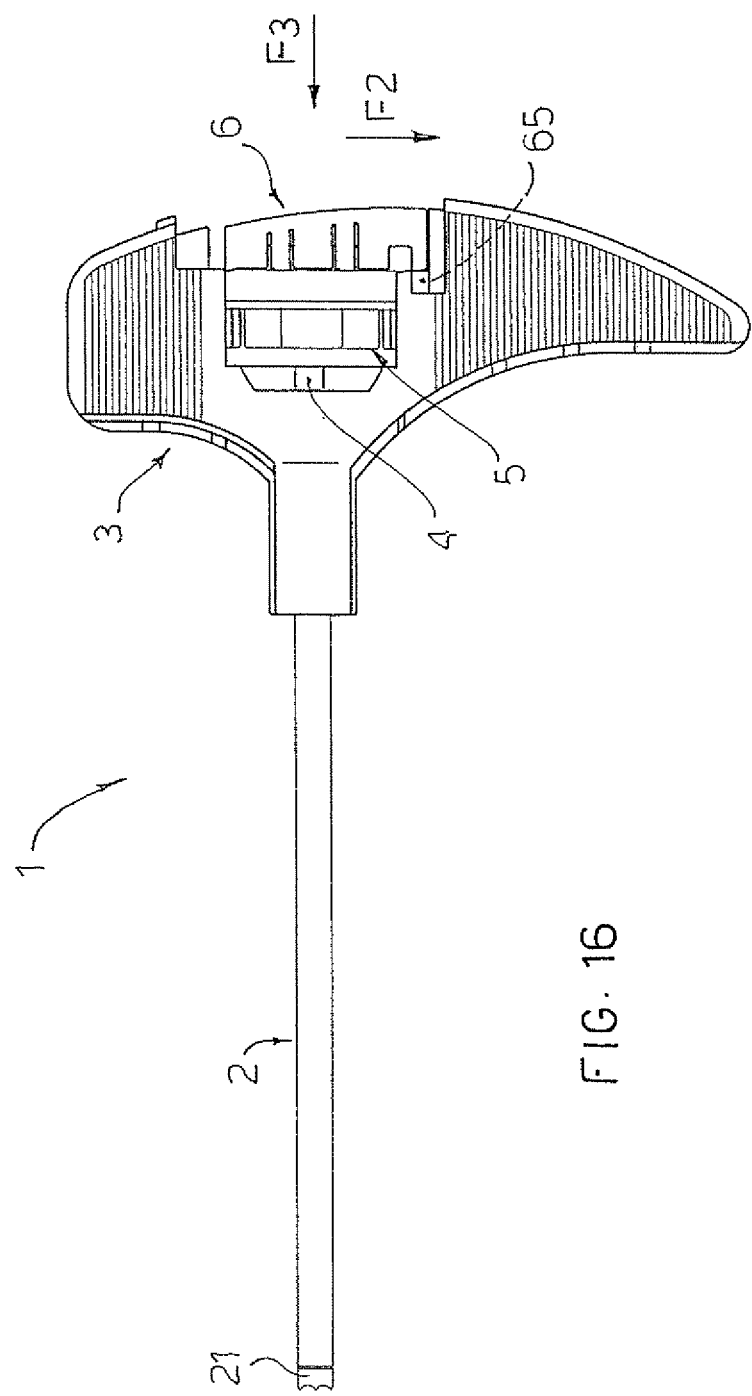
FIG. 16 is a side view of the bone biopsy device of FIG. 14, in which the stylet has been removed and the plate for collection of a sample of spongy bone has been activated.

As shown in FIG. 16, after resection of the frustule, the surgeon moves the latch 6 in the direction of the arrow F2, so as to bring the rib 65 of the latch level with the seat 37 of the handgrip, freeing the latch 6. The physician can then push the latch 6 in the axial direction of the arrow F3, at the same time also pushing the support 5 and the plate 4. The wings 52 of the support 5 bend elastically inwards and the groove 52' of the wings is snap released from the rib 36 of the guides 35 of the handgrip allowing the operator to push the support 5 integral with the plate 4 to its full extent with the latch 6. A click audible to the operator warns him that the distal end of the semi-cylindrical part 41 of the plate 4 has entered the mouth, reaching the end of its stroke and thus that the teeth 42 and 43 of the plate have gripped the base of the frustule.

Figure 17:
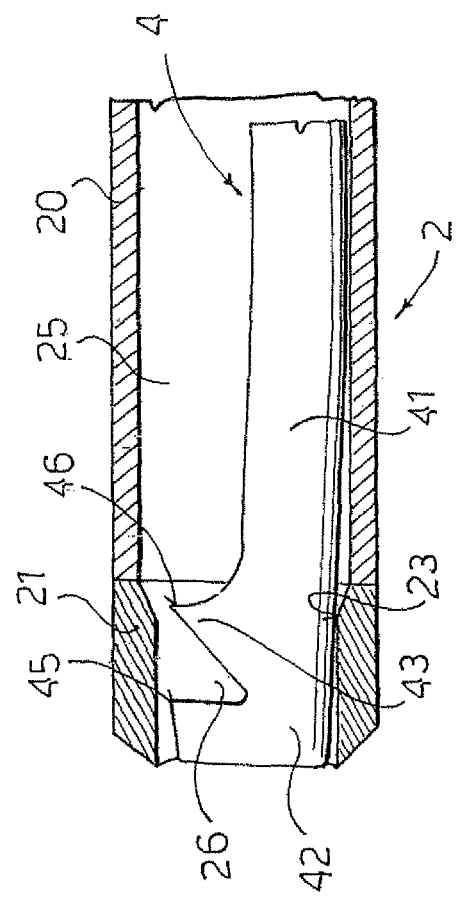
FIG. 17 is an enlarged view of the tip of the device of FIG. 16, in which the mouth of the cannula is shown in axial section.

As shown in FIG. 17, the semi-cylindrical part 41 of the plate 4 advances within the channel 25 of the cannula 2 and the circumferential teeth 42 and 43 disposed in the distal end of the semi-cylindrical part 41 of the plate bend radially inwards, when they encounter the tapered narrowing 23 defined by the mouth 21, acting as jaws which grip the base of the sectioned frustule. As a result the tips 45 and 46 of the teeth 42 and 43 come to clasp the base of the sectioned frustule firmly. The tapering of the narrowing 23 within the cannula ensures a gradual radial bending of the circumferential teeth 42 and 43.

The stylet 7 advantageously has a graduated scale section with notches 71 in its proximal portion. A compass (not shown in the drawings), which if needed will guide insertion of the stylet 7 into the tube 40 of the plate, will be provided as an accessory.

In this manner, before extraction of the plate 4, the operator if he wishes can check the length of the sectioned frustule by reinserting the stylet 7 into the instrument, possibly with the aid of the above mentioned guide compass, mounted in a proximal position on the latch 6, so as to read by how many notches 71 the stylet remains raised with respect to the compass.

At this point, the operator performs a rotation of the handgrip 3, severing the base of the frustule by twisting and subsequently pulls the support 5 of the plate axially. In this manner, the plate 4 is extracted from the cannula 2 and the sectioned frustule remains anchored to the semi-cylindrical part 41 of the plate, since the base of the frustule is retained firmly by the tips 45 and 46 of the teeth 42 and 43 of the plate. It should be noted that this operation leads to minimal damage to the frustule, only in the areas in which the frustule is clasped by the tips 45 and 46 of the teeth. Furthermore, frustule loss is practically nil, even in the most disparate cases of frustule consistency (almost liquid spongy bone or extremely hard spongy bone). It should be noted that this operation requires only axial advancement of the cannula 2, without any oscillatory luxating movement, to cause the necessary break at the base of the frustule.

Once the plate 4 has been extracted from the cannula 2, the frustule sample is removed from the cylindrical part 41 of the plate, possibly with the help of the tip 70 of the stylet 7. It should be noted that the device according to the invention does not require the use of a further instrument, such as a probe, for removal of the frustule sample.

Furthermore, with the device according to the invention it is possible to sample a very long frustule, with a length equal to about the length L2 of the semi-cylindrical part 41 of the plate, that is, a frustule greater than 2 cm, preferably about 3 cm. In this manner the relationship between the cortical portion and the spongy portion is more favourable for all the laboratory analyses required.

Figure 18:
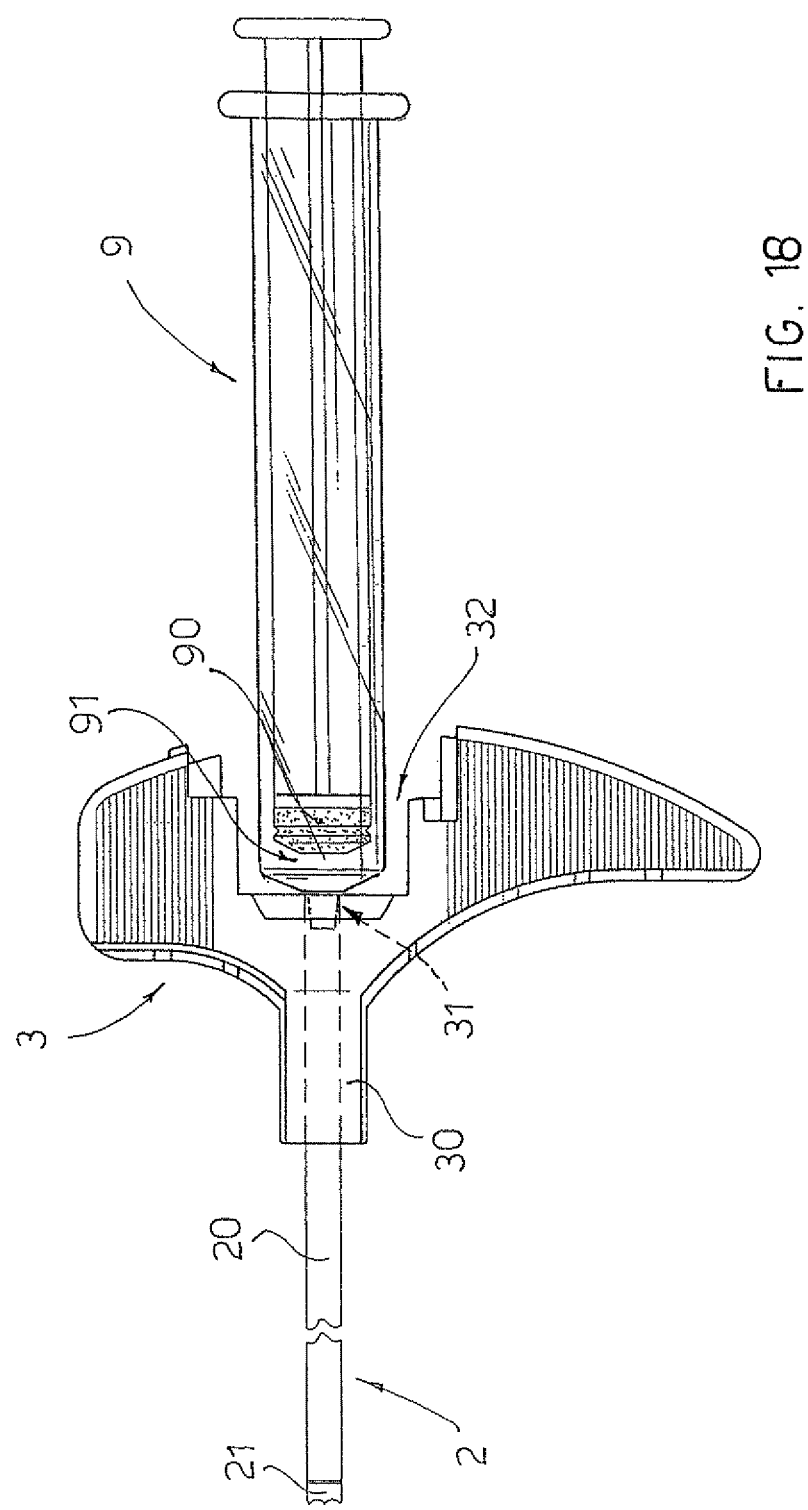
FIG. 18 is a side view of the bone biopsy device of FIG. 16, in which the plate has been removed and a syringe for collection of a bone marrow sample from the spongy bone has been attached.

During this operation of removing the frustule, the cannula 2 is left in place, since it can be used for sampling the blood marrow (blood) from the spongy part of the bone. In fact, as shown in FIG. 18, the operator can insert the tip of an aspirating medical device, such as a syringe 9, for example, into the Luer Lock cone 31 of the handgrip 3, afferent to the cannula 2. Then, by operating the piston 90 of the syringe, the blood present in the spongy part of the bone is aspirated, through the cannula 2, into the chamber 91 of the cylinder of the syringe 9.

It should be noted that the device 1 according to the invention makes it possible to carry out marrow sampling, after frustule sampling, thus without depriving the frustule of blood cells which are important for the analyses to be performed.

Numerous changes and modifications of detail within the reach of a person skilled in the art can be made to the present exemplifying embodiment of the invention without thereby departing from the scope of the invention as set forth in the appended claims.

The invention claimed is:

1. A bone biopsy device (1) comprising:
    an outer cannula (2) consisting of a cylindrical hollow tube (20) having a first outer diameter ($\phi 1$) and a first inner diameter ($\phi 2$), said cannula (2) being provided with a mouth (21) with a sharp cutting edge (27) to section a frustule of spongy bone, said mouth (21) being a hollow cylinder having a second outer diameter ($\phi 3$) and a second inner diameter ($\phi 4$), the second outer diameter ($\phi 3$) being equal to the first outer diameter ($\phi 1$);
    a plate (4) mounted slidably inside the cannula (2) and provided with a semi-cylindrical portion (41) at a distal end of the plate (4), said plate (4) being constructed and arranged to be initially disposed inside the outer cannula (2) in a compact mode corresponding to an orientation of the bone biopsy device (1) during bone perforation, and
    a stylet (7) mounted slidably inside the plate (4) and provided with a pointed tip (70) which protrudes from the mouth of the cannula (2) to pierce a compact part of the bone,
    wherein said sharp cutting edge (27) of the mouth (21) has a profile with a plurality of adjacent arcs of a circle, so as to define a plurality of tips (28) able to scratch and cut the bone thus resecting a cylindrical frustule of spongy bone, and
    wherein said mouth (21) of the cannula has on an inside portion a narrowing (23) and said semi-cylindrical part (41) of the plate has at the distal end at least a pair of opposed circumferential sets of teeth (42, 43) adapted to be bent radially inwards when they encounter said narrowing (23) of the mouth, so as to clasp firmly the base of the frustule previously sectioned by the cannula (2) as jaws and allow extraction of the frustule via the plate (4) whilst the cannula (2) is kept at the operating site.

2. The device (1) according to claim 1, wherein each tooth (42, 43) of the plate (4) comprises a tip (45, 46) adapted to penetrate the sectioned frustule.

3. The device (1) according to claim 2, wherein said plate (4) comprises a first pair of opposed teeth (42) disposed at the distal end thereof and a second pair of opposed teeth (43), wherein each tooth (42) of the first pair is separated from the respective tooth (43) of the second pair by a substantially V-shaped notch (44) formed in the semi-cylindrical portion (41) of the plate.

4. The device (1) according to claim 1, wherein said plate (4) comprises a first pair of opposed teeth (42) disposed at the distal end thereof and a second pair of opposed teeth (43), wherein each tooth (42) of the first pair is separated from the respective tooth (43) of the second pair by a substantially V-shaped notch (44) formed in the semi-cylindrical portion (41) of the plate.

5. The device (1) according to claim 4, wherein the teeth (42) of the first pair have a substantially trapezoidal profile and the teeth of the second pair (43) have a substantially triangular profile.

6. The device (1) according to claim 1, wherein said semi-cylindrical portion (41) of the plate has a length of 3 cm.

7. The device (1) according to claim 1, wherein said narrowing (23) of the mouth (21) of the cannula is tapered to allow gradual bending of the teeth (42, 43) of the plate.

8. The device (1) according to claim 1,
    wherein said mouth (21) is welded, by laser welding (22), to a distal edge of the cylindrical hollow tube (20) of the cannula,
    wherein the second inner diameter ($\phi 4$) is smaller than the second inner diameter ($\phi 2$) of the cannula, so as to define said narrowing (25) in the passage from the cannula tube to the mouth.

9. The device (1) according to claim 1, wherein the edge of the mouth (21) which is fixed, by laser welding (22), to the cylindrical hollow tube (20) of the cannula has a flared portion (23) which generates said tapered narrowing.

10. The device (1) according to claim 1, wherein said cannula (2) is joined to a metal cylinder by welding such as to make the cannula (2) integral with a handgrip (3).

11. A bone biopsy device (1) comprising:
- an outer cannula (2) provided with a mouth (21) with a cutting edge (27) to section a frustule of spongy bone,
- a plate (4) mounted slidably inside the cannula (2) and provided with a semi-cylindrical portion (41) at a distal end, and
- a stylet (7) mounted slidably inside the plate (4) and provided with a pointed tip (70) which protrudes from the mouth of the cannula (2) to pierce the compact part of the bone,
- wherein said mouth (21) of the cannula has on an inside a narrowing (23) and said semi-cylindrical part (41) of the plate has at the distal end at least a pair of opposed circumferential sets of teeth (42, 43) adapted to bend radially inwards when they encounter said narrowing (23) of the mouth, so as to clasp the base of the sectioned frustule and allow extraction of the frustule via the plate (4) whilst the cannula (2) is kept at the operating site
- wherein the device further comprises:
  - a handgrip (3) fixed to the proximal end of the cannula (2) by means of a metal cylinder joined thereto by welding,
  - a support (5) fixed to the proximal end of the plate (4),
  - a latch (6) mounted slidably on the support (5), and
  - a closing cover (8) fixed to the distal end of the stylet,
- wherein the handgrip (3) has a seat (32) adapted to accommodate said support (5) and said latch (6) and the closing cover (8) is adapted to be mounted on said latch (6).

12. The device (1) according to claim 11, wherein said latch (6) is mounted slidably on said support (5) to pass:
- from a closed position, wherein a rib (65) of the latch interferes with a wall (34') of the handgrip preventing it from being able to be pushed accidentally causing the plate (4) to advance prematurely within the cannula,
- to an open position, wherein said rib (65) of the latch is in register with a seat (37) of the handgrip allowing the latch to be pushed to allow the plate (4) to advance within the cannula.

13. The device (1) according to claim 12, wherein said handgrip (3) comprises:
- a cylindrical tang (30) in which a metal cylinder welded to the proximal end of the cannula (2) is fixed, and
- a frustoconical connector (31) of the Luer Lock type, disposed inside said tang (30) and accessible from said seat (32) of the handgrip to accommodate the tip of a medical aspiration instrument in order to aspirate the blood marrow from the spongy bone.

14. The device (1) according to claim 12, wherein said handgrip (3) has an ergonomic shape, comprising a first, shorter handgrip portion (33) and a second, longer handgrip portion (34) between which is formed said seat (32) to accommodate said support (5) of the plate and said latch (6) and said closing cover (8) of the stylet, joining the two handgrip portions (33, 34) whilst maintaining a continuity of the radius of curvature of the proximal surface of the handgrip.

15. The device (1) according to claim 12, wherein said stylet (7) has a graduated scale section with notches (71) in its proximal portion, to check the length of the sectioned frustule.

16. The device (1) according to claim 11, wherein said handgrip (3) comprises:
- a cylindrical tang (30) in which a metal cylinder welded to the proximal end of the cannula (2) is fixed, and
- a frustoconical connector (31) of the Luer Lock type, disposed inside said tang (30) and accessible from said seat (32) of the handgrip to accommodate the tip of a medical aspiration instrument in order to aspirate the blood marrow from the spongy bone.

17. The device (1) according to claim 16, wherein said handgrip (3) has an ergonomic shape, comprising a first, shorter handgrip portion (33) and a second, longer handgrip portion (34) between which is formed said seat (32) to accommodate said support (5) of the plate and said latch (6) and said closing cover (8) of the stylet, joining the two handgrip portions (33, 34) whilst maintaining a continuity of the radius of curvature of the proximal surface of the handgrip.

18. The device (1) according to claim 16, wherein said stylet (7) has a graduated scale section with notches (71) in its proximal portion, to check the length of the sectioned frustule.

19. The device (1) according to claim 11, wherein said handgrip (3) has an ergonomic shape, comprising a first, shorter handgrip portion (33) and a second, longer handgrip portion (34) between which is formed said seat (32) to accommodate said support (5) of the plate and said latch (6) and said closing cover (8) of the stylet, joining the two handgrip portions (33, 34) whilst maintaining a continuity of the radius of curvature of the proximal surface of the handgrip.

20. The device (1) according to claim 11, wherein said stylet (7) has a graduated scale section with notches (71) in its proximal portion, to check the length of the sectioned frustule.

* * * * *